(12) United States Patent
Evans et al.

(10) Patent No.: US 6,416,957 B1
(45) Date of Patent: Jul. 9, 2002

(54) METHOD FOR MODULATING PROCESS MEDIATED BY FARNESOID ACTIVATED RECEPTORS

(75) Inventors: Ronald M. Evans; Barry M. Forman, both of La Jolla, CA (US); Cary A. Weinberger, Carrboro, NC (US)

(73) Assignees: The Salk Institute for Biological Studies, La Jolla; Ligand Pharmaceuticals, Inc., San Diego, both of CA (US); The Government of the United States of America, Washington, DC (US)

( * ) Notice: Subject to any disclaimer, the term of this patent is extended or adjusted under 35 U.S.C. 154(b) by 62 days.

(21) Appl. No.: 09/696,443

(22) Filed: Oct. 24, 2000

Related U.S. Application Data

(62) Division of application No. 09/469,721, filed on Dec. 21, 1999, now Pat. No. 6,184,353, which is a division of application No. 08/372,183, filed on Jan. 13, 1995, now Pat. No. 6,005,086.

(51) Int. Cl.[7] .......................... G01N 33/53; C07K 14/00
(52) U.S. Cl. ......................................... 435/7.1; 530/350
(58) Field of Search ............................ 530/350; 435/7.1

(56) References Cited

U.S. PATENT DOCUMENTS 6,184,335 B1 * 2/2001 Evans et al. ................. 530/350

OTHER PUBLICATIONS

Bradley et al., "α and β thyroid hormone receptor (TR) gene expression during auditory neurogenesis: Evidence for TR isoform–specific transcriptional regulation in vivo" *Proc. Natl. Acad. Sci. USA* 91:439–443 (1994).

Brown and Goldstein, "Multivalent feedback regulation of HMG CoA reductase, a control mechanism coordinating isoprenoid synthesis and cell growth" *J. Lipid Res.* 21:505–517 (1980).

Danciger et al., "A Second Mouse Glutamic Acid Decarboxylase gene (Gad–2) Maps Proximal to Gad–1 on Chromosome 2" *Mouse Genome* 91:320–322 (1993).

Danielian et al., "Identification of a conserved region required for hormone dependent transcriptional activation by steroid hormone receptors" *EMBO J.* 11:1025–1033 (1992).

Edmond et al., "Mevalonate Metabolism: Role of Kidneys" *Science* 193:154–156 (1976).

Evans, "The Steroid and Thyroid Hormone Receptor Superfamily" *Science* 240:889–895 (1988).

Forman and Samuels, "Interactions Among a Subfamily of Nuclear Hormone Receptors: The Regulatory Zipper Model" *Mol. Endocrinol.* 4:1293–1301 (1990).

Glass, "Differential Recognition of Target Genes by Nuclear Receptor Monomers, Dimers, and Heterodimers" *Endocr. Rev.* 15:391–407 (1994).

Goldstein and Brown, "Regulation of the mevalonate pathway" *Nature* 343:425–430 (1990).

Gomez et al., "Purified yeast protein farnesyltransferase is structurally and functionally similar to its mammalian counterpart" *Biochem. J.* 289:25–31 (1993).

Göttlicher et al., "Fatty acids activate a chimera of the clofibric acid–activated receptor and the glucocorticoid receptor" *Proc. Natl. Acad. Sci. USA* 89:4653–4657 (1992).

Green and Wahli, "Peroxisome proliferator–activated receptors: finding the orphan a home" *Mol. Cell Endocrinol.* 100:149–153 (1994).

Hallenbeck et al., "Heterodimerization of thyroid hormone (TH) receptor with H–2RIIBP (RXRβ) enhances DNA binding and TH–dependent transcriptional activation" *Proc. Natl. Acad. Sci. USA* 89:5572–5576 (1992).

Heyman et al., "9–Cis Retinoic Acid Is a High Affinity Ligand for the Retinoid X Receptor" *Cell* 68:397–406 (1992).

Issemann and Green, "Activation of a member of the steroid hormone receptor superfamily by peroxisome proliferators" *Nature* 347:645–650 (1990).

Kensler et al., "Effects of Retinoic Acid and Juvenile Hormone on the Induction of Ornithine Decarboxylase Activity by 12–O–Tetradecanoylphorbol–13–acetate[1]" *Cancer Res.* 38:2896–2899 (1978).

Kim et al., "cDNA Cloning of MEV, a Mutant Protein That Facilitates Cellular Uptake of Mevalonate, and Identification of the Point Mutation Responsible for Its Gain of Function" *J. Biol. Chem.* 267:23223–23121 (1992).

Kliewer et al., "Retinoid X receptor interacts with nuclear receptors in retinoic acid, thyroid hormone and vitamin $D_3$ signalling" *Nature* 355:446–449 (1992).

Kurokawa et al., "Regulation of retinoid signalling by receptor polarity and allosteric control of ligand binding" *Nature* 371:528–531 (1994).

Leid et al., "Purification, Cloning, and RXR Identity on the HeLa Cell Factor with Which RAR or TR Heterodimerizes to Bind Target Sequences Efficiently" *Cell* 68:377–395 (1992).

Levin et al., "9–Cis retinoic acid stereoisomer binds and activates the nuclear receptor RXRα" *Nature* 355:359–361 (1992).

(List continued on next page.)

Primary Examiner—Karen Cochrane Carlson
(74) Attorney, Agent, or Firm—Stephen E. Reiter; Teresa Spehar; Foley & Lardner

(57) ABSTRACT

Farnesyl pyrophosphate, the metabolically active form of farnesol, is a key precursor in the synthesis of cholesterol, carotenoids, steroid hormones, bile acids and other molecules involved in cellular growth and metabolism. A nuclear receptor has been identified that is transcriptionally activated by farnesol and related molecules. This novel signaling pathway can be modulated by the use of key metabolic intermediates (or analogs and/or derivatives thereof) as transcriptional regulatory signals.

24 Claims, 6 Drawing Sheets

OTHER PUBLICATIONS

Mangelsdorf et al., "Characterization of three RXR genes that mediate the action of 9–cis retinoic acid" *Genes Dev.* 6:329–344 (1992).

Marks et al., "H–2RIIBP (RXRβ) heterodimerization provides a mechanism for combinatorial diversity in the regulation of retinoic acid and thyroid hormone responsive genes" *EMBO J.* 11:1419–1435 (1992).

Nagpal et al., "RARs and RXRs: evidence for two autonomous transactivation functions (AF–1 and AF–2) and heterodimerization in vivo" *EMBO J.* 12:2349–2360 (1993).

Nakanishi et al., "Multivalent Control of 3–Hydroxy–3–methylglutaryl Coenzyme A Reductase" *J. Biol. Chem.* 263:8929–8937 (1988).

O'Malley, "Editorial: Did Eucaryotic Steroid Receptors Evolve from Intracrine Gene Regulators?" *Endocrinology* 125:1119–1120 (1989).

Reiss et al., "Inhibition of Purified p21$^{ras}$ Farnesyl:Protein Transferase by Cys–AAX Tetrapeptides" *Cell* 62:81–88 (1990).

Righetti et al., "The in Vitro Metabolism of Mevalonate by Sterol and Non–sterol Pathways" *J. Biol. Chem.* 251:2716–2721 (1976).

Sunada et al., "Deficiency of Merosin in Dystrophic dy Mice and Genetic Linkage of Laminin M Chain Gene to dy Locus" *J. Biol. Chem.* 269:13729–13732 (1994).

Sutcliffe et al., "Control of Neuronal Gene Expression" *Science* 225:1308–1315 (1984).

Sze et al., "In Vitro Transcriptional Activation by a metabolic Intermediate: Activation by Leu3 Depends on α–Isopropylmalate" *Science* 258:1143–1145 (1992).

Thomas et al., "Heterodimerization of the Drosophila ecdysone receptor with retinoid X receptor and ultraspiracle" *Nature* 362:471–475 (1993).

Tomkins, "The Metabolic Code" *Science* 189:760–763 (1975).

Tontonoz et al., "mPPARγ2: tissue–specific regulator of an adipocyte enhancer" *Genes Dev.* 8:1224–1234 (1994).

Wang et al., "SREBP–1, a Membrane–Bound Transcription Factor Released by Sterol–Regulated Proteolysis" *Cell* 77:53–62 (1994).

Wiley et al., "The Quantitative Role of the Kidneys in the in Vivo Metabolism of Mevalonate" *J. Biol. Chem.* 252:548–554 (1977).

Yao et al., "Drosophila ultraspiracle Modulates Ecdysone Receptor Function via Heterodimer Formation" *Cell* 71:63–72 (1992).

Yao et al., "Functional ecdysone receptor is the product of EcR and Ultraspiracle genes" *Nature* 366:476–479 (1993).

Yu et al., "RXRβ: A Coregulator That Enhances Binding of Retinoic Acid, Thyroid Hormone, and Vitamin D Receptors to Their Cognate Response Elements" *Cell* 67:1251–1266 (1991).

Zhang et al., "Retinoid X receptor is an auxiliary protein for thyroid hormone and retinoic acid receptors" *Nature* 355:441–446 (1992).

Mangelsdorf, David J., et al., "Nuclear Receptor That Identifies a Novel Retinoic Acid Response Pathway," *Nature* 345:224–229 (1990).

Baes, Myriam, et al., A New Orphan Member of the Nuclear Hormone Receptor Superfamily That Interacts with a Subset of Retinoic Acid Response Elements, *Molecular and Cellular Biology* 14(3):1544–1552.

Seol, Wongi, et al., Isolation of Proteins That Interact Specifically with the Retinoid X Receptor: Two Novel Orphan Receptors, *Molecular Endocrinology* 9(1):72–85.

Shemshedini, Lirim et al., "Resistance to Juvenile Hormone and an Insect Growth Regulator in Drosophila is Associated with an Altered Cytosolic Juvenile Hormone–Binding Protein," *Proc. Natl. Acad. Sci. USA* 87(2072–2076).

* cited by examiner

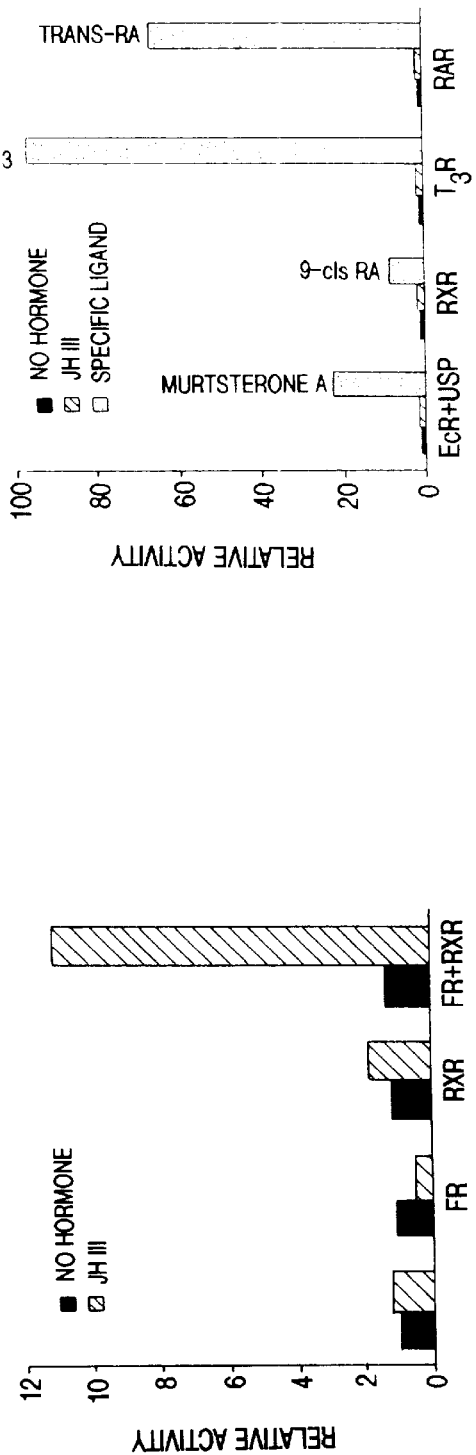
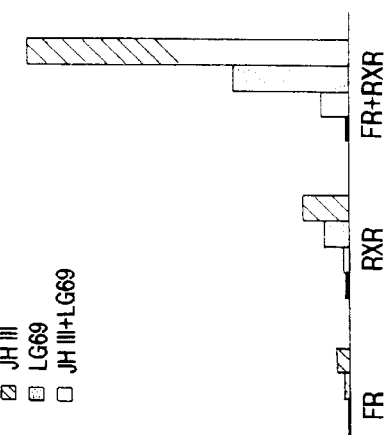
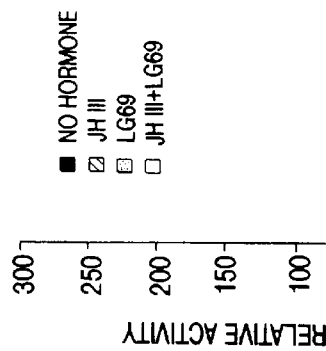
FIG. 5A
FIG. 5B
FIG. 5C

US 6,416,957 B1

METHOD FOR MODULATING PROCESS MEDIATED BY FARNESOID ACTIVATED RECEPTORS

This application is a divisional application of U.S. patent application Ser. No. 09/469,721, filed Dec. 21, 1999, now issued as U.S. Pat. No. 6,184,353, which is a divisional application of U.S. patent application Ser. No. 08/372,183, filed Jan. 13, 1995, now issued as U.S. Pat. No. 6,005,086.

FIELD OF THE INVENTION

The present invention relates to intracellular receptors, and ligands therefor. In a particular aspect, the present invention relates to methods for selectively modulating processes mediated by farnesoid activated receptors.

BACKGROUND OF THE INVENTION

Molecular cloning studies have demonstrated that receptors for steroids, retinoids, vitamin D and thyroid hormones comprise a superfamily of regulatory proteins that are structurally and functionally related (see Evans, in *Science* 240:889–895 (1988)). Known as nuclear receptors, these proteins bind to cis-acting elements in the promoters of their target genes and modulate gene expression in response to ligand therefor, such as a hormone.

Nuclear receptors can be classified based on their DNA binding properties (see Evans, supra and Glass, in *Endocr. Rev.* 15:391–407 (1994)). For example, the glucocorticoid, estrogen, androgen, progestin and mineralocorticoid receptors bind as homodimers to hormone response elements (HREs) organized as inverted repeats (IRs, see Glass, supra). A second class of receptors, including those activated by retinoic acid, thyroid hormone, vitamin $D_3$, fatty acids/peroxisome proliferators and ecdysone, bind to HREs as heterodimers with a common partner, the retinoid X receptor (i.e., RXR, also known as the 9-cis retinoic acid receptor; see, for example, Levin et al., in *Nature* 355:359–361 (1992) and Heyman et al., in *Cell* 68:397–406 (1992)).

An important advance in the characterization of the nuclear receptor superfamily of regulatory proteins has been the delineation of a growing number of gene products which possess the structural features of nuclear receptors, but which lack known ligands. Accordingly, such receptors are referred to as orphan receptors. The search for activators for orphan receptors has created exciting areas of research on previously unknown signaling pathways (see, for example, Levin et al., (1992), supra and Heyman et al., (1992), supra). Indeed, the ability to identify novel regulatory systems has important implications in physiology as well as human disease and methods for the treatment thereof.

Since receptors have been identified for all known nuclear-acting hormones, a question arises as to the types of molecules that may activate orphan receptors. In view of the fact that products of intermediary metabolism act as transcriptional regulators in bacteria and yeast, such molecules may serve similar functions in higher organisms (see, for example, Tomkins, in *Science* 189:760–763 (1975) and O'Malley, in *Endocrinology* 125:1119–1120 (1989)). For example, a crucial biosynthetic pathway in higher eucaryotes is the mevalonate pathway (see FIG. 1), which leads to the synthesis of cholesterol, bile acids, porphyrin, dolichol, ubiquinone, carotenoids, retinoids, vitamin D, steroid hormones and farnesylated proteins.

Farnesyl pyrophosphate (FPP), the metabolically active form of farnesol, represents the last precursor common to all branches of the mevalonate pathway (see FIG. 1). As a result, FPP is required for such fundamental biological processes as membrane biosynthesis, hormonal regulation, lipid absorption, glycoprotein synthesis, electron transport and cell growth (see Goldstein and Brown, in *Nature* 343:425–430 (1990)). Because of the central role of FPP in the production of numerous biologically important compounds, it is to be expected that its concentration should be closely regulated. This suggests that cells are likely to have developed strategies to sense and respond to changing levels of FPP, or its metabolites. One possible strategy by which cells can accomplish the desired regulation is to utilize a transcription factor whose activity is specifically regulated by a low molecular weight signaling molecule such as an FPP-like molecule. Potential candidates for such means to sense changing levels of FPP, or metabolites thereof, include members of the nuclear receptor superfamily, since these proteins are activated by low molecular weight signaling molecules.

BRIEF DESCRIPTION OF THE INVENTION

In accordance with the present invention, we have discovered that an orphan nuclear receptor, referred to as farnesoid activated receptor (i.e., FAR), is activated by farnesol and related molecules. Thus, FAR provides one of the first examples of a vertebrate transcription factor that is regulated by an intracellular metabolite. These findings suggest the existence of vertebrate signaling networks that are regulated by products of intermediary metabolism.

BRIEF DESCRIPTION OF THE FIGURES

FIGS. 5A, 5B and 5C demonstrate the hormonally controlled activity of the FAR-RXR complex. In FIG. 5A, the response of FAR alone, RXR alone and FAR+RXR to exposure to juvenile hormone III (JH III) is illustrated.

FIG. 5B illustrates the response of RXR alone, thyroid hormone receptor ($T_3R$) alone, RAR alone and ecdysone receptor+ultraspiracle (EcR+USP) to exposure to ligands selective for each respective receptor species (i.e., 100 nM $T_3$ (L-triiodothyronine), 1 μM trans-RA (all-trans-retinoic acid) or 100 nM muristerone A, respectively), or to JH III.

FIG. 5C illustrates the response of FAR alone, RXR alone and FAR+RXR to exposure to an FAR ligand (JH III), an RXR ligand (LG69, i.e., (4-{1–3,5,5,8,8-pentamethyl-5,6,7, 8-tetrahydro-2-napthalenyl)-1 -propenyl}benzoic acid), or a combination of JH III and LG69.

DETAILED DESCRIPTION OF THE INVENTION

In accordance with the present invention, a novel member of the nuclear receptor superfamily has been identified that forms heterodimers with RXR. The resulting FAR-RXR heterodimer complex is activated by farnesol and related metabolites. This FAR-RXR heterodimer binds to ecdysone-like response elements organized as an inverted repeat spaced by 1 nucleotide (referred to herein as IR1), a property that is unique among vertebrate nuclear receptors.

Thus, as described in greater detail in the Examples which follow, a degenerate 29-mer consensus oligonucleotide corresponding to the highly conserved P-box/DNA recognition helix (TCEGCK(G/V)FF; SEQ ID NO:1) of the nuclear receptor superfamily DNA binding domain (DBD) was used to probe a λgt11 cDNA library derived from mouse hepatoma Hepa-1c1c7 mRNA. Four positive cDNAs were identified from a low-stringency screen of two million clones and subjected to nucleotide sequence analysis. In addition to cDNAs for the previously described glucocorticoid and thyroid hormone receptors, two clones encoding novel orphan receptors were obtained. These cDNA clones were about 850 base pairs each and lacked complete coding sequences.

To obtain the complete open reading frame for OR2, a cDNA library from regenerating rat liver was screened. A 2.1 kb cDNA was cloned which encodes a 469 amino acid open reading frame (SEQ ID NO:2). In vitro translation of OR2.8 derived RNA results in a protein with a relative molecular mass ($M_r$) of 54,000, close to the predicted $M_r$ of 54,135. The OR2.8 cDNA contains a short interspersed repetitive DNA element (see Sutcliffe et al., in *Science* 225:1308–1315 (1984)) in the 3' untranslated region, followed by a polyadenylation signal. As described in detail herein, the OR2.8 cDNA encodes a novel member of the nuclear receptor superfamily that is activated by farnesoids. Accordingly, this novel receptor protein is referred to herein as FAR (Farnesoid Activated Receptor).

Figure 2:
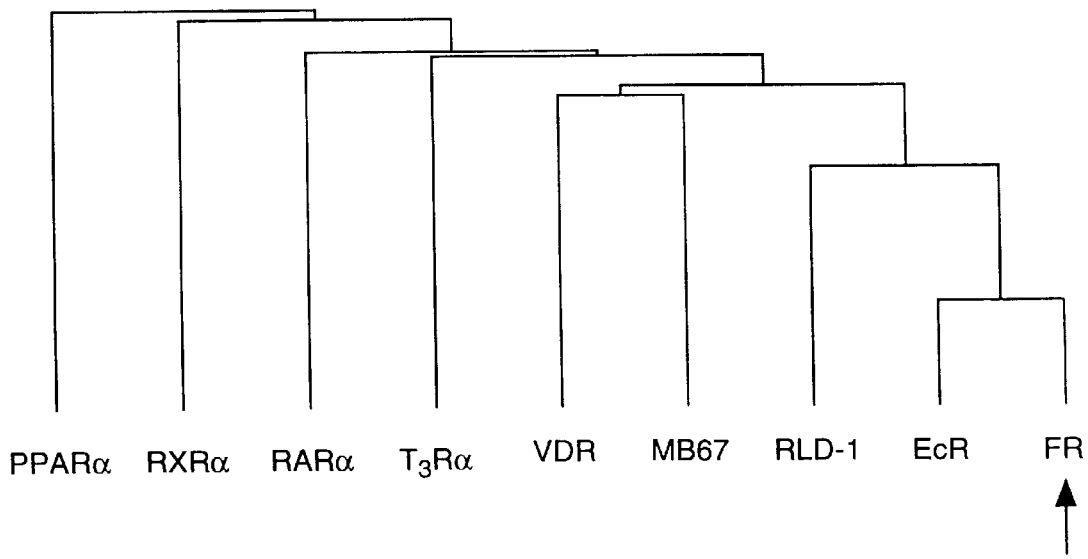
FIG. 2 summarizes the relationship among the DNA binding domains of FAR ($Cys^{124}$-$Met^{189}$) and other nuclear receptors (i.e., human peroxisome proliferator activated receptor (PPARα, Genbank L02932); human retinoid X receptor α (RXRα, Genbank X52773); human retinoic acid receptor α (RARα, Genbank X06538); human thyroid hormone receptor α1 ($T^3Rα$, Genbank M24748); human vitamin D receptor (VDR, Genbank J03258); human orphan nuclear receptor (MB67, Genbank L29263); rat orphan nuclear receptor (RLd-1, Genbank U11685); and Drosophila ecdysone receptor (EcR, Genbank M74078). Dendograms were created using the PILEUP program (Genetics Computer Group, version 7.2, University of Wisconsin)

Examination of the amino acid sequence of FAR confirms that it is a member of the nuclear receptor superfamily. The region spanning $Cys^{124}$-$Met^{289}$ contains several invariant amino acids, including 4 cysteine residues that are characteristic of the DNA binding domain (DBD) of all nuclear hormone receptors. The dendogram in FIG. 2 illustrates the relationship of this region to the DBD of other receptors. The FAR DBD is most similar to the DBD of the insect ecdysone receptor (EcR). These receptors share 81% amino acid sequence identity within their DBDs (see FIG. 3). The FAR DBD is more distantly related to other members of the nuclear receptor superfamily (see FIG. 2).

The carboxy-terminal ligand binding domain (LBD) of nuclear receptors is a complex region encoding subdomains for ligand binding, dimerization and transcriptional activation. Analysis of the carboxy terminal region in FAR (spanning $Leu^{250}$-$Gln^{469}$) indicates that it possesses only 33% sequence identity (59% similarity) with the corresponding region of the ecdysone receptor (see FIG. 3). Within this region, significant similarity is confined to regions involved in receptor dimerization (see Forman and Samuels, in *Mol. Endocrinol.* 4:1293–1301 (1990)), including the $T_i$ subdomain (48% identity), heptad repeats 4–6 (50% identity) and heptad 9 (75% identity). In addition, the last 22 amino acids, which possess transcriptional activation functions in other receptors (see Danielian et al., in *EMBO J.* 11:1025–1033 (1992)), are 42% identical among FAR and EcR (see FIG. 3). These structural similarities indicate that FAR is a member of the nuclear receptor superfamily with potential functional relatedness to the EcR.

As used herein, the phrase amino acid sequence similarity refers to sequences which have amino acid substitutions which do not change the inherent chemical properties of the subject polypeptide. Thus, amino acid sequences wherein an acidic residue is replaced with another acidic residue, or wherein a basic residue is replaced with another basic residue, or wherein a neutral residue is replaced with another neutral residue, retain a high degree of similarity with respect to the original sequence, notwithstanding the fact that the sequences are no longer identical.

Figure 1:
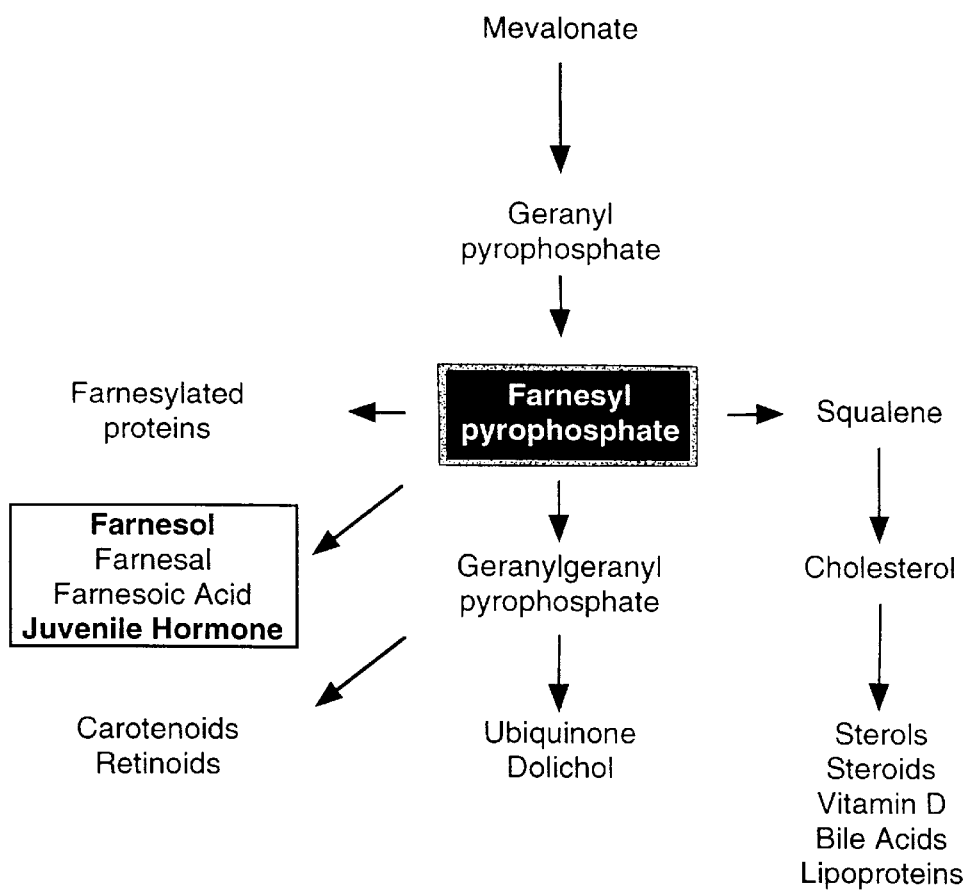
FIG. 1 illustrates the mevalonate pathway and details the relationship between FAR-RXR activators (set off in the figure by enclosure in a box) and the other compounds produced by the mevalonate pathway.

The ability to respond to metabolic intermediates distinguishes FAR from other nuclear receptors. FPP, the metabolically active form of farnesol, is a key metabolic precursor in the synthesis of numerous biologically active molecules including proteins (see FIG. 1 and Goldstein and Brown, in *Nature* 343:425–430 (1990).

Transcriptional regulation by intermediary metabolites such as carbohydrates, amino acids and lipids is a common paradigm in bacteria and yeast (see, for example, Sze et al., in *Science* 258:1143–1145 (1992)). In these systems the metabolite, or a related compound, often serves as an effector in a transcriptionally-regulated feedback loop that maintains appropriate concentrations of the metabolite/effector. The demonstration that FAR-RXR is regulated by farnesoid-related metabolites provides an example of this type of regulation in vertebrates.

Since farnesoid metabolites are synthesized intracellularly, individual cells which express FAR may also be producing the ultimate FAR activator. Other examples of transcriptional signaling by intracellular metabolites include the PPAR, a fatty acid-activated orphan receptor (see Gottlicher et al., in *Proc. Natl. Acad. Sci. USA* 89:4653–4657 (1992)) that regulates genes involved in fatty acid metabolism (see Green and Wahli, in *Mol. Cell Endocrinol.* 100:149–153 (1994)) and adipocyte differentiation (see Tontonoz et al., in *Genes Dev.* 8:1224–1234 (1994)). Similarly, the low density lipoprotein receptor gene regulator, SREBP-1, is maintained in an inactive form by hydroxycholesterol (see Wang et al., in *Cell* 77:53–62 (1994)). Together, these systems define a novel paradigm of metabolite-controlled intracellular (metacrine) signaling in vertebrates (see O'Malley, in *Endocrinology* 125:1119–1120 (1989). Metacrine signaling provides a means to regulate responses to intracellular metabolites in a cell-autonomous fashion. By transducing metabolic cues into genomic responses, FAR, PPAR and SREBP-1 provide examples of a metabolic code proposed by Gordon Tomkins in 1975 (see Tomkins, in *Science* 189:760–763 (1975)).

Activation of classical nuclear receptors occurs at physiological concentrations of circulating hormones, typically in the nanomolar range. However, the activation of PPAR by naturally occurring fatty acids requires 10–100 μM doses, consistent with the presumed intracellular concentration of these compounds. Physiologic concentrations of farnesoids have been difficult to determine due to their rapid metabolism and potential sequestration by intracellular and extracellular binding proteins.

Intracellular concentrations of farnesoids can be inferred from the Michaelis constant ($K_m$) of enzymes that utilize isoprenoid substrates. The $K_m$ of farnesyl:protein transferases for FPP ranges between 0.5 and 8.5 $\mu$M (see Gomez et al., in *Biochem. J.* 289:25–31 (1993) and Reiss et al., in *Cell* 62:81–88 (1990)) and half-maximal inhibition of isopentenyl pyrophosphate isomerase occurs with 10 $\mu$M FFP (see Rilling and Chayet, In: *Sterols and Bile Acids*, eds. Danielsson and Sjovall (Elsevier Science; 1985)). Furthermore, several biological effects of JH III and isoprenoids have been reported to occur in the 10–100 $\mu$M concentration range. For example, induction of ornithine decarboxylase by phorbol esters and phytohemagglutinin can be antagonized by 100 $\mu$M JH III in bovine lymphocytes (see Kensler et al., in *Cancer Res.* 38:2896–2899 (1978)). Similarly, down-regulation of HMG-CoA reductase activity by a mevalonate-derived non-sterol occurs when mevalonate is added to cells at concentrations in excess of 100 $\mu$M (see, for example, Brown and Goldstein, in *J. Lipid Res.* 21:505–517 (1980), and Nakanishi et al., in *J. Biol. Chem.* 263:8929–8937 (1988)). Moreover, FAR is expressed in the liver, intestine, adrenal gland and kidney: tissues known to support high flux through the mevalonate pathway. Thus, activation of FAR is likely to occur at appropriate farnesoid concentrations in physiologically relevant tissues.

FPP is known to regulate cell growth by virtue of its ability to alter the intracellular localization of ras and other proteins via covalent farnesylation (Goldstein and Brown, *Nature* 343:425–430 (1990)). The results presented herein suggest that in addition to this pathway, farnesoids are also capable of promoting biological changes through a novel transcriptional signaling pathway. Indeed, the identification of a farnesoid-dependent transcription factor provides the opportunity to modulate a key pathway responsible for the generation of lipids. Furthermore, the initial identification of a farnesoid-dependent transcription factor suggests that a network of farnesoid-responsive genes exist. Such genes can readily be identified by suitable means having the detailed information concerning FAR provided herein.

In accordance with the present invention, there is provided a method for modulating process(es) mediated by farnesoid activated receptor polypeptides, said method comprising conducting said process(es) in the presence of at least one farnesoid.

Farnesoid activated receptor polypeptides contemplated for use in the practice of the present invention can be characterized by reference to the unique tissue distribution thereof. Thus, expression of FAR polypeptides is restricted to the liver, gut, adrenal gland and kidney, all tissues known to have a significant flux through the mevalonate pathway.

Alternatively, farnesoid activated receptor polypeptides contemplated for use in the practice of the present invention can be characterized by:
  (1) being responsive to the presence of farnesoid(s) to regulate the transcription of associated gene(s);
  (2) having a relative molecular mass of about 54,000; and
  (3) having a DNA binding domain of about 66 amino acids with 9 Cys residues, wherein said DNA binding domain has:
    (a) about 81% amino acid identity with the DNA binding domain of the Drosophila ecdysone receptor,
    (b) about 56% amino acid identity with the DNA binding domain of VDR, and
    (c) about 45% amino acid identity with the DNA binding domain of hGR.

Farnesoid activated receptor polypeptides contemplated for use in the practice of the present invention can be further characterized by:
  (4) having a ligand binding domain of about 220 amino acids, wherein said ligand binding domain has:
    (a) about 33% amino acid identity, and about 59% amino acid similarity, with the ligand binding domain of the Drosophila ecdysone receptor,
    (b) about 32% amino acid identity with the ligand binding domain of VDR, and
    (c) about 26% amino acid identity with the ligand binding domain of hGR.

Presently preferred farnesoid activated receptor polypeptides contemplated for use in the practice of the present invention can be characterized as having substantially the same amino acid sequence as that shown in SEQ ID NO:2. Especially preferred farnesoid activated receptor polypeptides contemplated for use in the practice of the present invention are those which have the same amino acid sequence as that shown in SEQ ID NO:2.

The phrase "substantially the same" is used herein in reference to amino acid sequences that have slight and non-consequential sequence variations from the actual sequences disclosed herein. Species which are "substantially the same as the reference sequence are considered to be equivalent to the disclosed sequences and as such are within the scope of the appended claims.

Farnesoid compounds contemplated for use in the practice of the present invention include compounds having the structure:

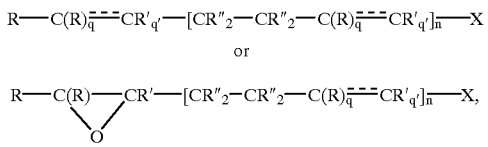

wherein
  each R is independently lower alkyl or alkoxy,
  each R' is independently selected from hydrogen, lower alkyl or alkoxy,
  each R" is independently selected from hydrogen, lower alkyl or alkoxy,
  X is selected from —CH$_2$OH, —CH$_2$OAc, —CO$_2$H, or —CO$_2$Me,
  n is 2 or 3,
  each q is independently 1 or 2,
  each q' is independently 1 or 2, and
  q and q' are the same.

Exemplary farnesoids contemplated for use in the practice of the present invention include those wherein:
  (1) each R is methyl, each R' is hydrogen, each R" is hydrogen, X is —CH$_2$OH, n is 2, and each q and q' is 1 (i.e., the farnesoid molecule is polyunsaturated);
  (2) each R is methyl, each R' and each R" is hydrogen, X is —CO$_2$H, n is 2, and each q and q' is 1 (i.e., the farnesoid molecule is polyunsaturated);
  (3) the polyene backbone of the farnesoid molecule contains an epoxide functionality, each R is methyl, each R' is hydrogen, each R" is hydrogen, X, is —CH$_2$Me, n is 2, and each q and q' is 1;
  (4) each R is methyl, each R' is hydrogen, each R" is hydrogen, X is —OAc, n is 2, and each q and q' is 1;

(5) each R is methyl, each R' is hydrogen, each R" is hydrogen, X is —CH$_2$OH, n is 3, and each q and q' is 1; and the like.

In accordance with another embodiment of the present invention, there is provided a method of testing a compound for its ability to regulate transcription-activating effects of a farnesoid activated receptor polypeptide, said method comprising assaying for reporter protein when cells containing a farnesoid activated receptor polypeptide and reporter construct are contacted with said compound;

wherein said reporter construct comprises:
(a) a promoter that is operable in said cell,
(b) a hormone response element, and
(c) DNA encoding a reporter protein,
wherein said reporter protein-encoding DNA segment is operatively linked to said promoter for transcription of said DNA segment, and
wherein said promoter is operatively linked to said hormone response element for activation thereof.

The invention will now be described in greater detail by reference to the following non-limiting examples.

EXAMPLE 1

Cloning of FAR

A degenerate 29-mer consensus oligonucleotide (5'-ACC TGT GAG GGC TGC AAR GKY TTC TTC AA-3'; SEQ ID NO:3), corresponding to the highly conserved P-box/DNA recognition helix (TCEGCK(G/V)FF; SEQ ID NO:1) of the nuclear receptor superfamily DNA binding domain (DBD) was used to probe a λgt11 mouse hepatoma Hepa-1c1c7 cDNA library of 2×10$^6$ clones under low stringency conditions (see Issemann and Green, in *Nature* 347:645–650 (1990)). An incomplete 850 bp mouse OR2 cDNA clone was obtained. This clone was used subsequently to screen a regenerated rat liver cDNA library.

A full length clone (referred to as OR2.8) was obtained from this screen and sequenced by the dideoxy sequencing method. The deduced amino acid sequence thereof is presented herein as SEQ ID NO:2.

EXAMPLE 2

Formation of FAR-RXR Complexes

Figure 3:
FIG. 3 presents an amino acid sequence comparison between rat FAR and Drosophila EcR. Similarity between the DNA binding and ligand binding domains are schematically represented as percent amino acid identity. Amino acid regions comprising each domain are numbered accordingly.

In order to explore the functional properties of FR, the DNA binding properties of this orphan receptor were analyzed. It has previously been shown that RXR is a common heterodimeric partner required for high affinity DNA binding by several nuclear receptors (see, for example, Hallenbeck et al., in *Proc. Natl. Acad. Sci. USA* 89:5572–5576 (1992); Kliewer et al., in *Nature* 355:446–449 (1992); Leid et al., in *Cell* 68:377–395 (1992); Marks et al., in *EMBO J.* 11:1419–1435 (1992); Yu et al., in *Cell* 67:1251–1266 (1991); and Zhang et al,. in *Nature* 355:441–446 (1992). Moreover, it has been shown that the DNA and ligand binding activities of the Drosophila ecdysone receptor (EcR) require heterodimer formation with RXR or USP (the Drosophila homologue of RXR; see O'Malley in *Endocrinology* 125:1119–1120 (1989)). As illustrated in FIG. 3, FAR and EcR possess striking similarity within the dimerization subdomain of the ligand binding domain (LBD). Furthermore, FAR is colocalized with sites of RXRα and RXRβ expression (see Example 6 below). These observations prompted an investigation as to whether FAR could interact with RXR, or with other members of the nuclear receptor superfamily. To do so, a two-hybrid system modified for use in mammalian cells was employed (see, for example, Nagpal et al., in *EMBO J.* 12:2349–2360 (1993)).

Figure 4:
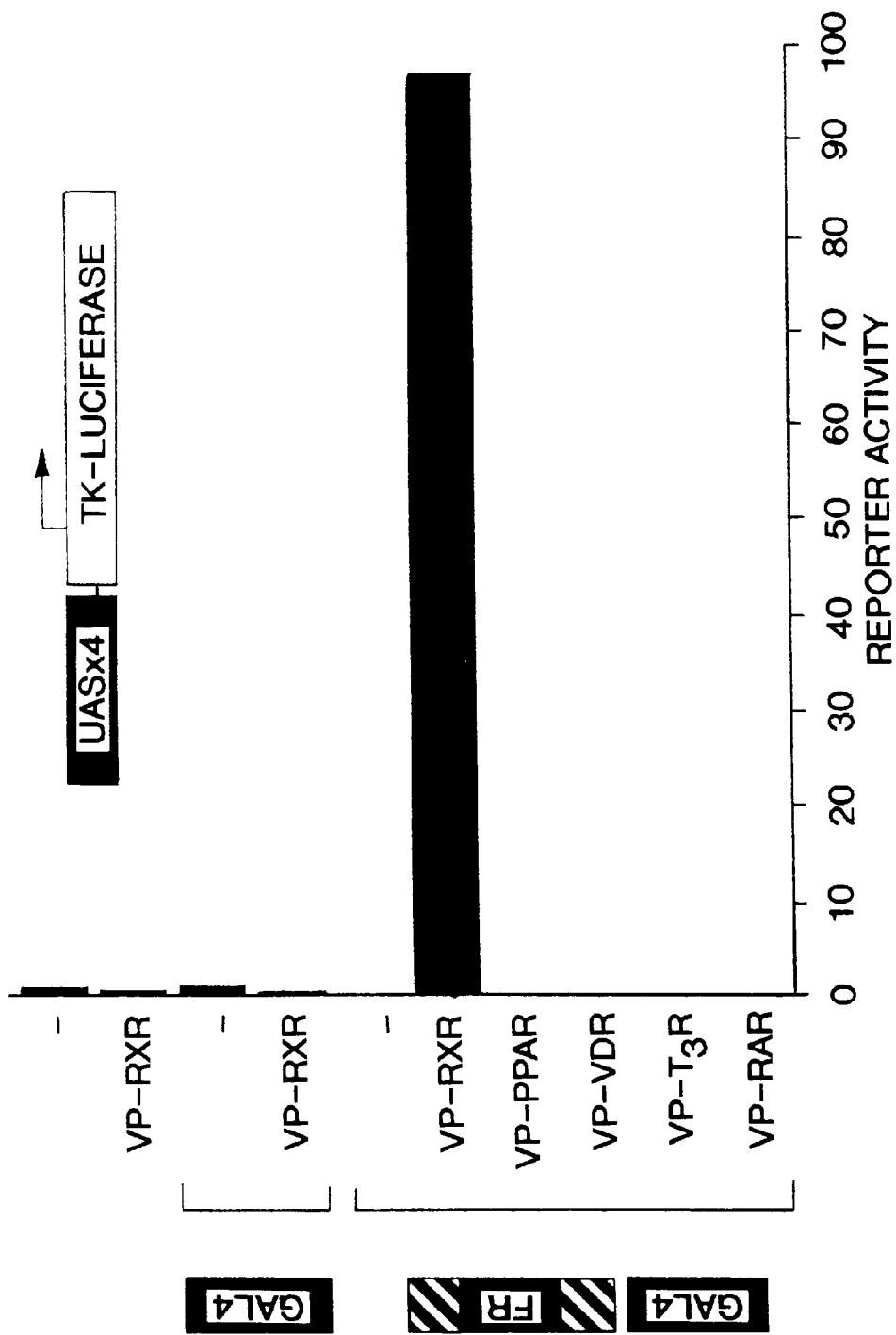
FIG. 4 demonstrates the interaction of FAR and RXR.

Thus, CV-1 cells were transiently transfected (as indicated in FIG. 4) with cytomegalovirus promoter driven expression vectors containing the yeast GAL4 DNA binding domain (DBD) alone (GAL4$_{1-147}$), GAL4 linked to the FAR ligand binding domain (LBD; i.e., GAL4-FAR$_{184-469}$), and the 78 amino acid Herpes virus VP16 transactivation domain (VP) linked to the amino terminal end of the LBDs for human RXRα (VP-RXR$_{203-462}$), mouse PPARα (VP-PPAR$_{155-468}$), VDR (VP-VDR$_{92-427}$), T$_3$Rβ (VP-T$_3$Rβ$_{173-456}$) or RARα (VP-RAR$_{156-462}$). All cells were cotransfected with a luciferase reporter construct containing 4 copies of the yeast GAL4 upstream activating sequence and a β-galactosidase expression vector as internal control.

Thus, CV-1 cells were grown in DMEM supplemented with 10% AG1-X8 resin-charcoal stripped calf bovine serum, 50 U/ml penicillin G and 50 µg/ml streptomycin sulfate (DMEM-CBS) at 37° C. in 5% CO$_2$. One day prior to transfection, cells were plated to 50–80% confluence using phenol-red free DEEM with 10% resin charcoal stripped fetal bovine serum (DMEM-FBS). Cells were transfected (with reporter construct (300 ng/10$^5$ cells), cytomegalovirus driven receptor (100 ng/10$^5$ cells) and β-galactosidase expression vectors (500 ng/10$^5$ cells) as indicated in FIG. 4) by lipofection using N-{2-(2,3)-dioleoyloxy)propyl-N,N,N -trimethyl ammonium methyl sulfate} according to the manufacturer's instructions (DOTAP, Boehringer Mannheim). After 2 hours the liposomes were removed and cells treated for 40 hours with phenol-red free DMEM-FBS containing farnesol as the ligand. Cells were harvested and assayed for luciferase and β-galactosidase activity. All points were performed in triplicate and varied by less than 10%. Experiments were repeated three or more time with similar results. Data points were normalized for differences in transfection efficiency using β-galactosidase, and plotted as relative activity where the untreated reporter is defined to have an activity of 1 unit.

As seen in FIG. 4, neither the GAL4 DBD, nor the GAL4-FAR chimera are capable of stimulating transcription from a reporter construct containing the GAL4 upstream activating sequence. Similarly, a fusion protein containing the Herpes virus VP16 transactivation domain linked to the RXRα-LBD (VP-RXR) is inactive when expressed alone or with the GAL4 DBD. However, when GAL4-FAR and VP-RXR are coexpressed, the reporter is dramatically activated (by about 500-fold), indicating that FAR and RXRα interact efficiently in cells. Using similar VP16-LBD fusion proteins, no interaction could be detected between FAR and receptors for peroxisome proliferators/fatty acids (PPAR), vitamin D$_3$ (VDR), thyroid hormone (T$_3$R), retinoic acid (RAR) or other members of the nuclear receptor superfamily. These data indicate that the LBDs of FAR and RXRα associate in a highly specific fashion.

The only combination resulting in significant activation was GAL4-FAR+VP-RXR. As one would expect (based on previous in vitro studies (see Hallenbeck et al., supra and Zhang et al, supra)), VP-PPAR, VP-VDR, VP-T$_3$R and VP-PPAR interacted productively with GAL4-RXR, thereby confirming that these VP16 chimeras are functionally expressed.

EXAMPLE 3

Binding of FAR-RXR Complexes to DNA

It was next sought to determine the DNA binding properties of the FAR-RXRα complex. Because FAR and EcR share 100% sequence identity in the DNA recognition helix (P-box, Cys[141]-Lys[145]), it was examined whether the FAR-RXRα complex could recognize the hsp27 element response element (EcRE; Yao et al., Cell 71:63–72 (1992)). Electrophoretic mobility shift analysis was performed using [$^{32}$P]-labeled DNA and in vitro translated FAR and RXRα. Proteins used in electrophoretic mobility shift assays were prepared by translation in a rabbit reticulocyte lysate system (TNT, Promega). Proteins (1 μl) were incubated for 20 minutes at room temperature with 100,000 cpm of Klenow-labeled probes in 10 mM Tris pH 8, 100 mM KCl, 6% glycerol, 0.05% NP-40, 1 mM DTT, 100 ng/μl poly dI dC and then electrophoresed through a 5% polyacrylamide gel in 0.5× TBE. The gel was autoradiographed for 1.5 hours with an intensifying screen.

Neither FR nor RXRα alone were capable of high affinity binding to the hsp27-EcRE. However, when mixed, the two proteins bound cooperatively to the hsp27-EcRE (GGTTCA A TGCACT; SEQ ID NO:4). Binding to this element is specific as indicated by the inability of the FAR-RXRα complex to recognize a mutated 11N-hsp27-EcRE (EcRE$_m$; CGTTCA A TGCACA; SEQ ID NO:5).

The hsp27-EcRE consists of two imperfect core binding sites arranged as inverted repeats separated by 1 nucleotide (IR1; SEQ ID NO:4). Accordingly, the binding of FAR-RXRα was further examined on an idealized IR1 containing two consensus half-sites (AGGTCA A TGACCT; SEQ ID NO:6). The FAR-RXRα complex was also found to bind cooperatively to the idealized IR1, but not to a mutant IR1 containing substitutions within the half-sites (IR1$_m$; AGAACA A TGTTCT; SEQ ID NO:7). Thus, FAR-RXRα binds to ecdysone-like IR1 response elements, and represents the first vertebrate receptor complex to possess this property.

EXAMPLE 4

Activation by Farnesoids

It was next sought to determine whether FAR possessed transcriptional activity that could be hormonally controlled. Based on the identification of an EcRE as a DNA target, a reporter plasmid was constructed containing 5 copies of the hsp27 response element linked to a truncated mouse mammary tumor virus promoter (Yao et al., Nature 366:476–479 (1993)). This reporter was cotransfected into CV-1 cells alone, or with expression vectors for FAR and/or RXRα. Cotransfected cells were treated with a variety of potential ligands and monitored for changes in luciferase activity.

Transient transfections were performed as described in Example 3 using reporter constructs (300–1000 ng/10$^5$ cells), cytomegalovirus driven receptor (50 ng/10$^5$ cells', and β-galactosidase expression vectors (500 ng/10$^5$ cells) as indicated in FIGS. 5A, 5B and 5C.

Thus, with reference to FIG. 5A, CV-1 cells were transiently transfected with hsp27-EcRE×5 MTV-luciferase alone (−) or with expression vectors for rat FAR and/or human RXRα. Reporter activity was assayed after treating cells with or without 50 μM JH III. FIG. 5A illustrates that JH III elicited a dramatic induction (10-fold) of luciferase activity in cells expressing both FAR and RXRα, relative to cells expressing either FAR or RXRα alone. It is of note that JH III failed to activate FAR-RXR complexes using the parental MTV reporter construct, which lacked the EcREs.

In contrast to the demonstrated ability of JH III to activate FAR-RXR complexes (see FIG. 5A), JH III fails to activate other nuclear receptors other than FAR, as shown in FIG. 5B. Thus, the activity of the following receptor/luciferase reporter pairs were assayed in the presence of 50 μM JH III or the indicated receptor-specific ligand: Drosophila G-EcR+USP/hsp27-EcRE×5 MTV; human RXRα/CRBPII-TK; human T$_3$Rβ/TREp×2-TK; and human RARα/DR5×2-TK.

As seen in FIG. 5C, the FAR-RXR complex is synergistically activated by JH III and LG69 (i.e., (4-{1-3,5,5,8,8-pentamethyl-5,6,7,8-tetrahydro-2-napthalenyl)-1-propenyl}benzoic acid). CV-1 cells were transiently transfected as described above with reference to FIG. 5A, but treated with or without 50 μM JH III, 100 nM LG69 and JH III+LG69.

Unexpectedly, JH III (50 μM) elicited a dramatic induction (10-fold) of luciferase activity in cells expressing both FAR and RXRα (FIG. 5A). Other potential ligands including steroids, retroretinoids, eicosanoids and bile acids had no effect. JH III appears to be specific for the FAR-RXRα complex since it failed to activate the. ecdysone (EcR+USP), 9-cis retinoic acid (RXR), thyroid hormone (T$_3$R) or all-trans retinoic acid receptors (RAR) (FIG. 5B).

Although JH III activates FR-RXRα, it fails to activate either FR or RXRα alone (FIGS. 5A and 5B). This is similar to observations with the Drosophila EcR, which requires formation of an EcR/USP or EcR/RXR complex for transcriptional activity (see, for example, Yao et al., in Nature 366:476–479 (1993); Yao et al., in Cell 71:63–72 (1992); and Thomas et al., in Nature 362:471–475 (1993)). EcR itself binds ecdysteroids with low affinity (Yao et al., (1993), supra; high affinity binding and subsequent transcriptional activation requires coexpression of EcR with RXR or USP. Thus, while the EcR/RXR-USP heterodimer is the physiologically active complex, the ability to respond to ecdysone is determined by the EcR component of the complex. Since the EcR-RXR heterodimer is composed of two functional receptors, the complex can be activated independently by ecdysteroids or 9-cis retinoic acid, and synergistically by both ligands (Kensler et al., in Cancer Res. 38:2896–2899 (1978)).

The structural and functional similarities between EcR and FAR prompted an examination of whether the FAR-RXRα complex could also be synergistically activated by JH III and an RXR-specific ligand (such as LG69; see Kurokawa et al., in Nature 371:528–531 (1994)). Thus, using the hsp27 EcRE reporter, the FAR-RXRα complex was activated 17-fold by 50 μM JH III, 76-fold by 100 nM LG69 and 212-fold by the combination of JH III and LG69. This synergistic activity required coexpression of FAR with RXRα, RXRβ or RXRλ. The ability of JH III to synergize with saturating doses of LG69 or 9-cis RA suggests that these two compounds have distinct targets within the FAR-RXR complex. Since LG69 has previously been shown to be an RXR-specific ligand, these results imply that JH III responsiveness is determined by the FAR component of the FAR-RXR complex.

EXAMPLE 5

Evaluation of Mevalonate Metabolites as FAR Ligands

Figure 6A:
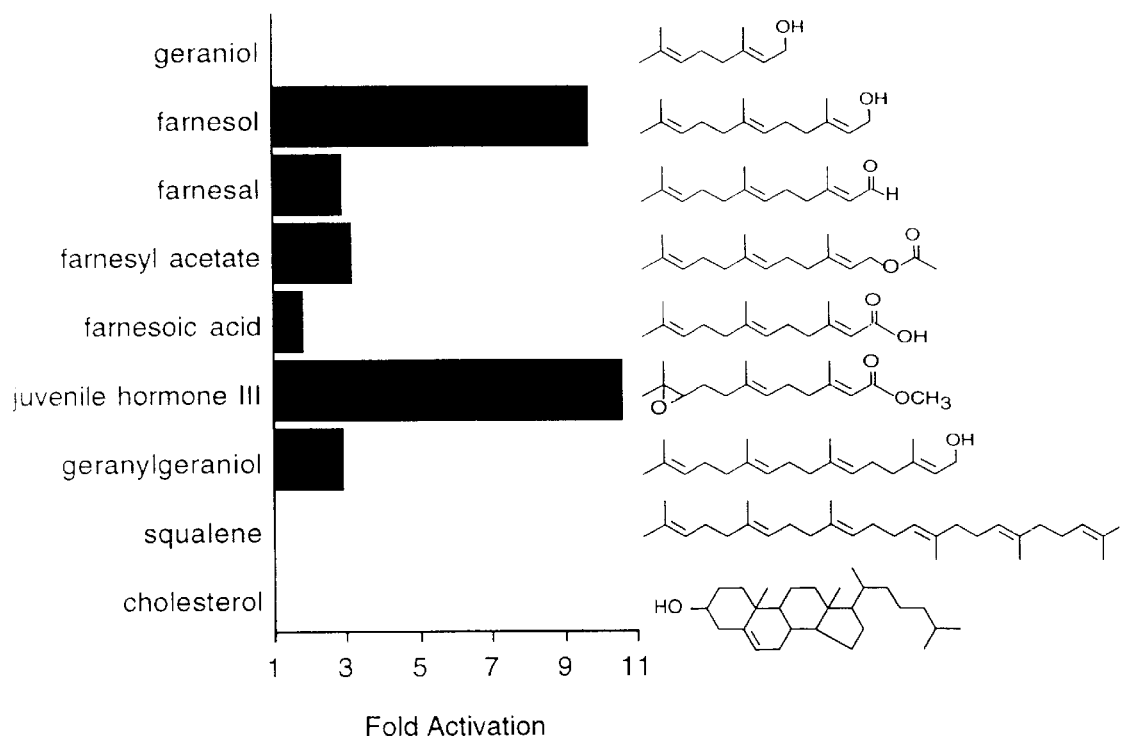
FIG. 6A summarizes FAR-RXR activity when exposed to various isoprenoids.

JH III (cis-10,11-epoxy-3,7,11-trimethyl-trans-trans-2,6-dodecadienoic acid methyl ester) is a metabolic derivative of farnesyl pyrophosphate (FPP; 3,7,11-trimethyl-2,6,10-dodecatrien-1-ol-pyrophosphate (see FIG. 6A). FPP is derived from the mevalonate biosynthetic pathway and is itself a precursor in the synthesis of other biologically active compounds (see FIG. 1, and Goldstein and Brown, in *Nature* 343:425–430. (1990). Accordingly, it was decided to test whether metabolites derived from the mevalonate pathway in mammalian cells could also serve as activators of the FAR-RXRα complex.

Mevalonate can be synthesized de novo from acetyl CoA and is metabolized into farnesyl pyrophosphate (FPP), the metabolically active form of farnesol. FPP serves as a key intermediate in that it represents a critical branch point in the mevalonate pathway. Accordingly, metabolites of FPP contribute to a number of essential cellular processes. The results presented herein indicate that the FAR-RXR nuclear receptor complex responds most efficiently to farnesol and juvenile hormone III. These findings suggest that metabolic intermediates are capable of serving as transcriptional regulators in animal cells. Based on the results presented herein, it is likely that the FAR-RXR complex plays a central role in a feedback loop that serves to regulate the synthesis of enzymes within the mevalonate pathway.

Thus, CV-1 cells were transiently transfected with expression vectors for rat FR and human RXRα, as described above in Example 3. Cells were treated with 50 μM concentrations of farnesol and/or farnesol metabolites. Data is plotted in FIG. 6A as fold activation relative to untreated cells. Similar results were obtained with all-trans retinoic acid and mixed isomers of farnesol and farnesoic acid.

Figure 6B:
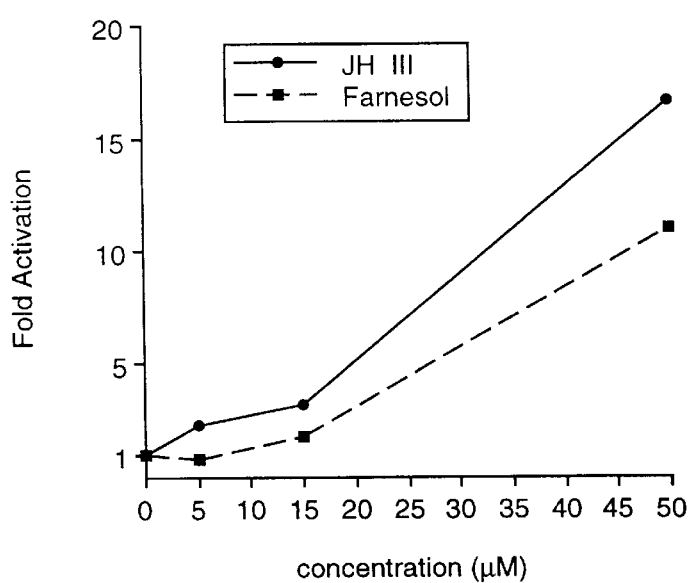
FIG. 6B presents a dose-response profile for exposure of FAR-RXR complex to JH III and farnesol.

FIG. 6B presents a dose-response profile for the two most effective activators observed in the evaluation described in FIG. 6A, i.e., JH III and farnesol. The experiments were performed as described above for FIG. 6A, with the concentration of JH III and farnesol (mixed isomers) indicated in the FIG. Activation required concentrations in the range of 5–50 μM.

Remarkably, farnesol (trans-trans or mixed isomers, 50 μM) was observed to be a strong activator of FAR-RXRα (see FIG. 6A), whereas other farnesoids, such as farnesal, farnesyl acetate and geranylgeraniol, possessed weaker activity. In contrast, little or no activation was seen with 50 μM concentrations of geraniol, farnesoic acid, squalene, methoprene, mevalonate, squalene epoxide, squalene dioxide, lanosterol, 24,25-epoxycholesterol, pregnenolone, dehydroepiandrosterone, bile acids or 10 μM 25-hydroxycholesterol. Mevalonate (200 μM) displayed weak activity, provided cells were cotransfected with a mevalonate transporter protein (see Kim et al., in *J. Biol. Chem.* 267:23223–23121 (1992)).

EXAMPLE 6

Expression of FAR mRNA

One expectation of an intracellular metabolic activator is that it would be synthesized in the same tissues where its receptor is expressed. Accordingly, the expression of FAR in rat tissues was examined by Northern blot analysis. For Northern analysis, polyA$^+$ RNA (10 μg) from various rat tissues was electrophoresed through a 1% agarose gel under denaturing conditions and transferred to a filter. The filter was hybridized to the mouse FAR truncated cDNA that was [$^{32}$P]-labeled by the random primer method (see Mangelsdorf et al., *Genes Dev.* 6:329–344 (1992); 5×10$^8$ cpm/μg). This probe corresponds to rat FAR sequences spanning amino acids 1–297 which encode the N-terminus, the DNA binding domain (DBD) and a portion of the ligand binding domain (LBD) of FR.

Hybridization was performed overnight at 65° C. in 500 mM sodium phosphate (dibasic:monobasic, 7:3), 1 mM ethylenediaminetetraacetic acid, 1% bovine serum albumin and 7% sodium dodecyl sulfate. The filter was washed twice in 2×SSC(1×SSC is 0.15 M NaCl, 0.015 M sodium citrate) at room temperature, twice in 1×SSC at 55° C. and then autoradiographed with an intensifying screen at −70° C. for 5 days. In situ hybridizations were performed as described by Bradley et al., in *Proc. Natl. Acad. Sci. USA* 91:439–443 (1994). Sections were apposed to Kodak X-OMAT film for 10 days, and then coated with nuclear emulsion and exposed for 16 weeks.

A single transcript of 2.3 kb was observed only in liver and kidney. No significant expression was detected in the brain, heart, lung, skeletal muscle, pancreas, skin, spleen or testis.

In situ hybridization/histochemistry was performed to further localize sites of FAR expression. Antisense cRNA probes from truncated mouse FAR cDNA or full-length mouse RXRβ cDNA were used. The control was a truncated rat glucocorticoid receptor sense cRNA probe. The control probe revealed near-background hybridization.

FAR transcripts were restricted to the liver, kidney and gut of rat embryonic day 19.5 (E19.5) embryo sections. Near background levels were seen in other tissues and in experiments using a control probe. As one might expect (see Mangelsdorf et al., in *Genes Dev.* 6:329–344 (1992)), mRNA for the heterodimerizing partner RXRβ is also found in the liver, kidney and gut, as well as other embryonic tissues. FAR expression in the gut is prominent in the intestinal villi. In the E19.5 kidney, expression is heterogeneous, with highest FAR levels confined to the renal tubules. In the adult kidney, high levels of expression of FAR are seen in areas rich in renal tubules: the medullary rays and medullary stripe. FAR expression is also detected in the adrenal cortex of the adult mouse. Thus, FAR expression is restricted to the liver, gut, adrenal gland and kidney: tissues known to have significant flux through the mevalonate pathway (see, for example, Edmond et al., in *Science* 193:154–156 (1976); Righetti et al., in *J. Biol. Chem.* 251:2716–2721 (1976); and Wiley et al., in *J. Biol. Chem.* 252:548–554 (1977)).

EXAMPLE 7

FAR Gene Family

The chromosomal location of mouse FAR was determined by analysis of 2 multilocus genetic crosses for inheritance of polymorphic FAR gene fragments (see Danciger et al., in *Mouse Genome* 91:320–322.(1993), and Sunada et al., in *J. Biol. Chem.* 269:13729–13732 (1994)).

Thus, truncated mouse FAR cDNA was used as a probe to analyze 2 multilocus genetic crosses for inheritance of polymorphic Fxr gene fragments: (NFS/N or C58/J×M. m musculus and (NFS/N×M. spretus)×M spretus or C58/J. DNA from the progeny of these crosses have been typed for approximately 700 markers including the Chr 10 markers Pfp (pore forming protein), Tra1 (tumor rejection antigen gp96), Ifg (interferon γ), Gli (glioma associated oncogene) and Gad1-ps1 (glutamic acid decarboxylase 1 pseudogene).

To the right of the map (FIG. 7) are the recombination fractions between adjacent loci; percent recombination and standard errors are shown in parentheses. Human map locations for the homologues of individual genes are indicated to the left of the map.

To determine whether there may be related genes that comprise a FR gene family, Southern blot analysis of rat genomic DNA was performed and the patterns obtained under high and low stringency hybridization were compared. Thus, duplicate samples of Lewis rat DNA (10 μg) were digested with a variety of restriction enzymes and electrophoresed through a 1% agarose gel. DNA was digested with restriction enzyme, transferred to a nitrocellulose filter and then hybridized with the [$^{32}$P]-labeled mouse FAR truncated cDNA probe under high or low stringency conditions. As one might expect, high stringency conditions revealed a limited number of specific bands for each restriction enzyme. Under low stringency conditions, many additional bands were obtained, suggesting the existence of one or more FAR-related genes in the rat genome. Although further analysis is required to determine whether these related sequences are functionally expressed, these findings raise the possibility that additional farnesoid activated receptors will be identified.

Figure 7:
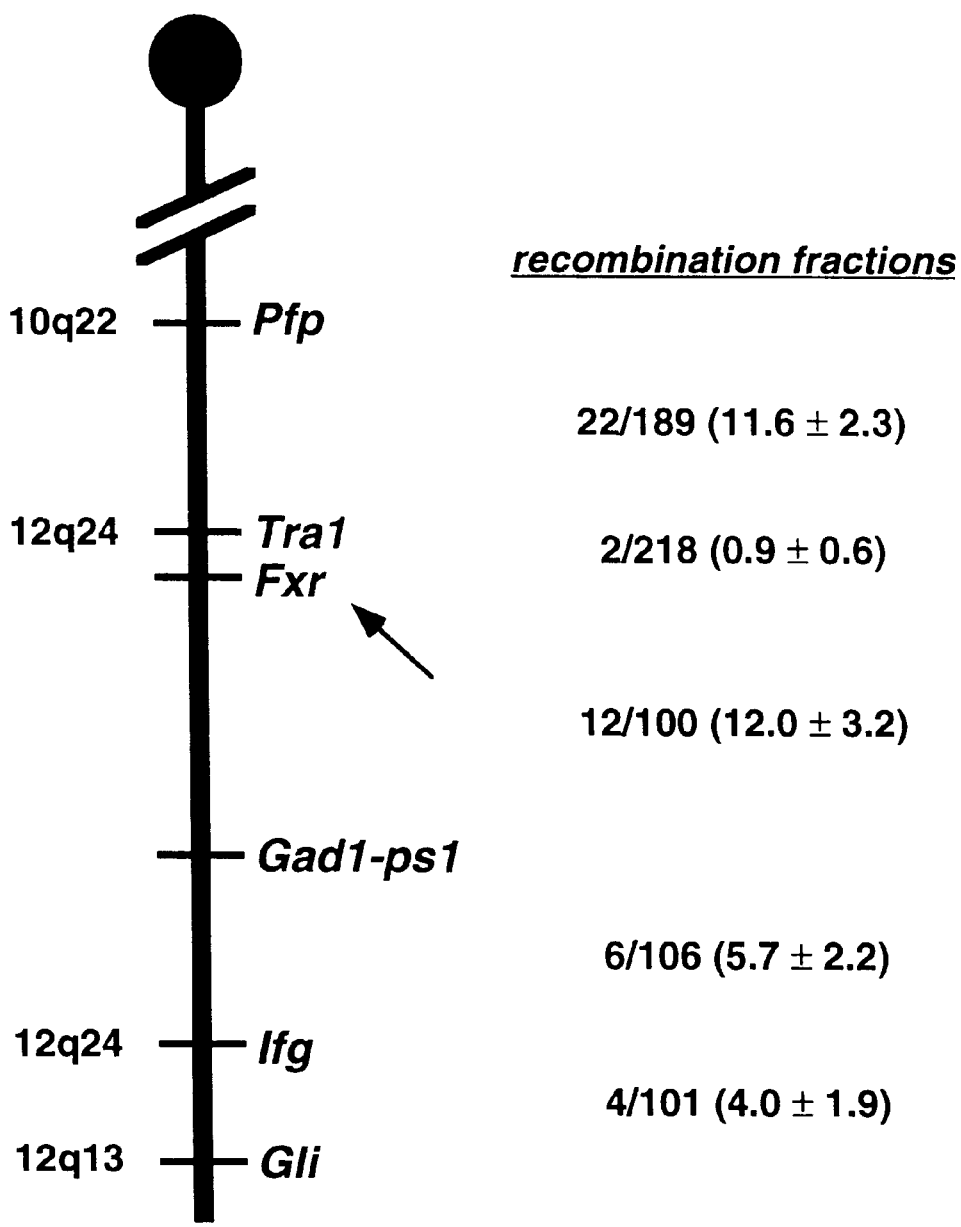
FIG. 7 is an abbreviated genetic map showing the localization of the Fxr gene on mouse Chr 10.

Southern analysis revealed HindIII digested fragments of 7.5 kb, 6.0 kb and 3.0 kb in NFS/N mouse DNA and 25.0, 7.5 and 3.0 kb in M. spretus. ScaI digestion produced fragments of 23.1 kb in NFS/N and 28 kb in M. m.musculus. The inheritance of these fragments demonstrated that Fxr, the gene encoding FR, is localized near the Tra1 locus on mouse Chromosome 10 (FIG. 7). This map location is within a region of conserved linkage with human chromosome 12q suggesting a possible map location for human Fxr.

While the invention has been described in detail with reference to certain preferred embodiments thereof, it will be understood that modifications and variations are within the spirit and scope of that which is described and claimed.

That which is claimed is:

1. A method of testing a compound for its ability to activate a farnesoid-activated receptor (FAR) polypeptide,
   wherein said receptor polypeptide is a nuclear receptor and is responsive to the presence of farnesoid to regulate the transcription of genes having response elements organized as an IR1, said method comprising assaying for a reporter protein when cells containing said receptor polypeptide and a reporter construct are contacted with said compound,
   wherein said reporter construct comprises
      a) a promoter that is operable in said cell,
      b) a response element organized as an IR1,
      c) a DNA encoding a reporter protein,
      wherein said DNA is operatively linked to said promoter for transcription of said DNA and said promoter is operatively linked to said response element for activation thereof; and
   wherein said activation of said receptor polypeptide results in transcription and expression of the reporter protein.

2. A method according to claim 1, wherein said receptor polypeptide is further characterized by reference to the unique tissue distribution thereof, wherein expression of FAR polypeptides is restricted to the liver, gut, adrenal gland and kidney.

3. A method according to claim 1, wherein said receptor polypeptide is further characterized by having:
   (1) a relative molecular mass of about 54,000 Daltons; and
   (2) a DNA binding domain of about 66 amino acids with 9 Cys residues, wherein said DNA binding domain is encoded by a nucleic acid sequence that hybridizes under low stringency conditions of 42° C. for 24 hours with 0 or 10% formamide, 1×Denhardt's solution, 6×NET 0.2% SDS, and 100 µg/ml denatured salmon sperm DNA, and washed four times for 20 minutes at 25° C. in 2×SSC, 0.1% SDS to a nucleic acid molecule encoding amino acid residues 124–189 set forth in SEQ ID NO:2; and
   (3) a ligand binding domain.

4. A method according to claim 3, wherein said ligand binding domain is further characterized by being about 220 amino acids.

5. A method according to claim 4, wherein said ligand binding domain is encoded by a nucleic acid sequence that hybridizes under low stringency conditions of 42° C. for 24 hours with 0 or 10% formamide, 1×Denhardt's solution, 6×NET 0.2% SDS, and 100 µg/ml denatured salmon sperm DNA, and washed four times for 20 minutes at 25° C. in 2×SSC, 0.1% SDS to a nucleic acid molecule encoding amino acid residues 250–469 set forth in SEQ ID NO:2.

6. A method according to claim 1, wherein said receptor polypeptide is encoded by DNA that hybridizes under low stringency conditions of 42° C. for 24 hours with 0 or 10% formamide, 1×Denhardt's solution, 6×NET 0.2% SDS, and 100 µg/ml denatured salmon sperm DNA, and washed four times for 20 minutes at 25° C. in 2×SSC, 0.1% SDS to a DNA encoding the amino acid sequence shown in SEQ ID NO:2.

7. A method according to claim 1, wherein said receptor polypeptide has the same amino acid sequence as that shown in SEQ ID NO:2.

8. A method of testing a compound for its ability to activate a farnesoid-activated receptor (FAR) polypeptide,
   wherein said receptor polypeptide is a nuclear receptor and is responsive to the presence of farnesoid to regulate the transcription of genes having response elements organized as an IR1,
   said method comprising assaying for a reporter protein when cells containing a chimeric receptor polypeptide comprising the ligand binding domain of said receptor polypeptide and a heterologous DNA binding domain, a reporter construct, and optionally a retinoid X receptor, are contacted with said compound,
   wherein said reporter construct comprises
      a) a promoter that is operable in said cell,
      b) a response element recognizable by the DNA binding domain of said chimeric receptor polypeptide,
      c) a DNA encoding a reporter protein,
      wherein said DNA is operatively linked to said promoter for transcription of said DNA and said promoter is operatively linked to said response element for activation thereof; and
   wherein activation of said chimeric receptor polypeptide results in transcription and expression of the reporter protein, thereby identifying a compound that activates said receptor polypeptide.

9. A method of testing a compound for its ability to inhibit a farnesoid-activated receptor (FAR) polypeptide,
   wherein said receptor polypeptide is a nuclear receptor and is responsive to the presence of farnesoid to regulate the transcription of genes having response elements organized as an IR1, said method comprising contacting cells which contain said receptor polypeptide, a reporter construct, and optionally a retinoid X receptor (RXR), with at least one FAR agonist and optionally a RXR agonist, in the absence or presence of said compound,
   wherein said reporter construct comprises
      a) a promoter that is operable in said cell,
      b) a response element organized as an IR1,
      c) a DNA encoding a reporter protein,
      wherein said DNA is operatively linked to said promoter for transcription of said DNA and said promoter is operatively linked to said response element for activation thereof; and
   wherein said inhibition of said receptor polypeptide in the presence of said compound results in reduced transcription and expression of the reporter protein relative to that observed in the absence of said compound.

10. A method according to claim 9, wherein said receptor polypeptide is further characterized by reference to the unique tissue distribution thereof, wherein expression of FAR polypeptides is restricted to the liver, gut, adrenal gland and kidney.

11. A method according to claim 9, wherein said receptor polypeptide is further characterized by having:
   (1) a relative molecular mass of about 54,000 Daltons; and
   (2) a DNA binding domain of about 66 amino acids with 9 Cys residues, wherein said DNA binding domain is encoded by a nucleic acid sequence that hybridizes under low stringency conditions of 42° C. for 24 hours with 0 or 10% formamide, 1×Denhardt's solution, 6×NET 0.2% SDS, and 100 µg/ml denatured salmon sperm DNA, and washed four times for 20 minutes at 25° C. in 2×SSC, 0.1% SDS to a nucleic acid molecule encoding amino acid residues 124–189 set forth in SEQ ID NO:2; and
   (3) a ligand binding domain.

12. A method according to claim 11, wherein said ligand binding domain is further characterized by being about 220 amino acids.

13. A method according to claim 12, wherein said ligand binding domain is encoded by a nucleic acid sequence that hybridizes under low stringency conditions of 42° C. for 24 hours with 0 or 10% formamide, 1×Denhardt's solution, 6×NET 0.2% SDS, and 100 µg/ml denatured salmon sperm DNA, and washed four times for 20 minutes at 25° C. in 2×SSC, 0.1% SDS to a nucleic acid molecule encoding amino acid residues 250–469 set forth in SEQ ID NO:2.

14. A method according to claim 9, wherein said receptor polypeptide is encoded by DNA that hybridizes under low stringency conditions of 42° C. for 24 hours with 0 or 10% formamide, 1×Denhardt's solution, 6×NET 0.2% SDS, and 100 µg/ml denatured salmon sperm DNA, and washed four times for 20 minutes at 25° C. in 2×SSC, 0.1% SDS to a DNA encoding the amino acid sequence shown in SEQ ID NO:2.

15. A method according to claim 9, wherein said receptor polypeptide has the same amino acid sequence as that shown in SEQ ID NO:2.

16. A method according to claim 9, wherein said agonist is a farnesoid.

17. A method according to claim 16, wherein said farnesoid has the structure:

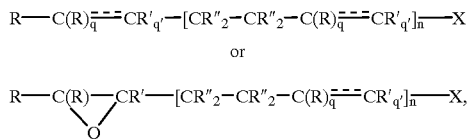

wherein
each R is independently lower alkyl or alkoxy,
each R' is independently selected from hydrogen, lower alkyl or alkoxy,
each R" is independently selected from hydrogen, lower alkyl or alkoxy,
X is selected from —CH$_2$OH, —CH$_2$OAc, —CO$_2$H, or —CO$_2$Me,
n is 2 or 3,
each q is independently 1 or 2,
each q' is independently 1 or 2, and
q and q' are the same.

18. A method according to claim 17, wherein each R is methyl, each R' is hydrogen, each R" is hydrogen, X is —CH$_2$OH, n is 2, and each q and q' is 1.

19. A method according to claim 17, wherein each R is methyl, each R' is hydrogen, each R" is hydrogen, X is —CO$_2$H, n is 2, and each q and q' is 1.

20. A method according to claim 17, wherein the polyene backbone contains an epoxide functionality, each R is methyl, each R' is hydrogen, each R" is hydrogen, X is —CH$_2$Me, n is 2, and each q and q' is 1.

21. A method according to claim 17, wherein each R is methyl, each R' is hydrogen, each R" is hydrogen, X is —OAc, n is 2, and each q and q' is 1.

22. A method according to claim 17, wherein each R is methyl, each R' is hydrogen, each R" is hydrogen, X is —CH$_2$OH, n is 3, and each q and q' is 1.

23. A method according to claim 9, wherein said compound is a putative antagonist for said receptor polypeptide, and wherein said contacting is carried out in the presence of
  increasing concentrations of said compound,
  and a fixed concentration of at least one agonist for said receptor polypeptide.

24. A method of testing a compound for its ability to inhibit a farnesoid-activated receptor (FAR) polypeptide,
  wherein said receptor polypeptide is a nuclear receptor and is responsive to the presence of farnesoid to regulate the transcription of genes having response elements organized as an IR1,
  said method comprising contacting cells containing a chimeric receptor polypeptide comprising the ligand binding domain of said receptor polypeptide and a heterologous DNA binding domain, a reporter construct, and optionally a retinoid X receptor (RXR), with at least one FAR agonist and optionally a RXR agonist, in the absence or presence of said compound,
  wherein said reporter construct comprises
    a) a promoter that is operable in said cell,
    b) a response element recognizable by the DNA binding domain of said chimeric receptor polypeptide,
    c) a DNA encoding a reporter protein,
    wherein said DNA is operatively linked to said promoter for transcription of said DNA and said promoter is operatively linked to said response element for activation thereof; and
  wherein inhibition of said chimeric receptor polypeptide in the presence of said compound results in reduced transcription and expression of the reporter protein relative to that observed in the absence of said compound, thereby identifying a compound that inhibits said receptor polypeptide.

* * * * *

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 9 amino acids
      (B) TYPE: amino acid
      (D) TOPOLOGY: linear (ii) MOLECULE TYPE: protein (v) FRAGMENT TYPE: internal (ix) FEATURE:
      (A) NAME/KEY: Modified-site
      (B) LOCATION: 7
      (D) OTHER INFORMATION: /note= "Xaa at position 7 is either
         a glycine (G) or valine (V)."

(xi) SEQUENCE DESCRIPTION: SEQ ID NO: 1:

Thr Cys Glu Gly Cys Lys Xaa Phe Phe
1               5

(2) INFORMATION FOR SEQ ID NO: 2:

(i) SEQUENCE CHARACTERISTICS:
      (A) LENGTH: 469 amino acids
      (B) TYPE: amino acid
      (D) TOPOLOGY: linear (ii) MOLECULE TYPE: protein (xi) SEQUENCE DESCRIPTION: SEQ ID NO: 2:

Met Asn Leu Ile Gly Pro Ser His Leu Gln Ala Thr Asp Glu Phe Ala
1               5                   10                  15

Leu Ser Glu Asn Leu Phe Gly Val Leu Thr Glu His Ala Ala Gly Pro
                20                  25                  30

Leu Gly Gln Asn Leu Asp Leu Glu Ser Tyr Ser Pro Tyr Asn Asn Val
            35                  40                  45

Gln Phe Pro Gln Val Gln Pro Gln Ile Ser Ser Ser Ser Tyr Tyr Ser
        50                  55                  60

Asn Leu Gly Phe Tyr Pro Gln Gln Pro Glu Asp Trp Tyr Ser Pro Gly
65                  70                  75                  80

Leu Tyr Glu Leu Arg Arg Met Pro Thr Glu Ser Val Tyr Gln Gly Glu

```
                      85                  90                    95
Thr Glu Val Ser Glu Met Pro Val Thr Lys Lys Pro Arg Met Ala Ala
                100                 105                 110
Ser Ser Ala Gly Arg Ile Lys Gly Asp Glu Leu Cys Val Val Cys Gly
            115                 120                 125
Asp Arg Ala Ser Gly Tyr His Tyr Asn Ala Leu Thr Cys Glu Gly Cys
        130                 135                 140
Lys Gly Phe Phe Arg Arg Ser Ile Thr Lys Asn Ala Val Tyr Lys Cys
145                 150                 155                 160
Lys Asn Gly Gly Asn Cys Val Met Asp Met Tyr Met Arg Arg Lys Cys
                165                 170                 175
Gln Asp Cys Arg Leu Arg Lys Cys Arg Glu Met Gly Met Leu Ala Glu
            180                 185                 190
Cys Leu Leu Thr Glu Ile Gln Cys Lys Ser Lys Arg Leu Arg Lys Asn
        195                 200                 205
Val Lys Gln His Ala Asp Gln Thr Val Asn Glu Asp Ser Glu Gly Arg
    210                 215                 220
Asp Leu Arg Gln Val Thr Ser Thr Thr Lys Leu Cys Arg Glu Lys Thr
225                 230                 235                 240
Glu Leu Thr Val Asp Gln Gln Thr Leu Leu Asp Tyr Ile Met Asp Ser
                245                 250                 255
Tyr Ser Lys Gln Arg Met Pro Gln Glu Ile Thr Asn Lys Ile Leu Lys
            260                 265                 270
Glu Glu Phe Ser Ala Glu Glu Asn Phe Leu Ile Leu Thr Glu Met Ala
        275                 280                 285
Thr Ser His Val Gln Ile Leu Val Glu Phe Thr Lys Arg Leu Pro Gly
    290                 295                 300
Phe Gln Thr Leu Asp His Glu Asp Gln Ile Ala Leu Leu Lys Gly Ser
305                 310                 315                 320
Ala Val Glu Ala Met Phe Leu Arg Ser Ala Glu Ile Phe Asn Lys Lys
                325                 330                 335
Leu Leu Pro Asp Thr Gln Thr Cys Trp Lys Lys Glu Phe Glu Arg Ala
            340                 345                 350
Ala Ser Pro Met Arg Tyr Ile Thr Pro Met Phe Ser Phe Tyr Lys Ser
        355                 360                 365
Val Gly Glu Leu Lys Met Thr Gln Glu Glu Tyr Ala Leu Leu Thr Ala
    370                 375                 380
Ile Val Ile Leu Ser Pro Asp Arg Gln Tyr Ile Lys Asp Arg Glu Ala
385                 390                 395                 400
Val Glu Lys Leu Gln Glu Pro Leu Leu Asp Val Leu Gln Lys Leu Cys
                405                 410                 415
Lys Ile Tyr Gln Pro Glu Asn Pro Gln His Phe Ala Cys Leu Leu Gly
            420                 425                 430
Arg Leu Thr Glu Leu Arg Thr Phe Asn His His His Ala Glu Met Leu
        435                 440                 445
Met Ser Trp Arg Val Asn Asp His Lys Phe Thr Pro Leu Leu Cys Glu
    450                 455                 460
Ile Trp Asp Val Gln
465
```

(2) INFORMATION FOR SEQ ID NO: 3:

(i) SEQUENCE CHARACTERISTICS:
        (A) LENGTH: 29 base pairs (B) TYPE: nucleic acid
        (C) STRANDEDNESS: single
        (D) TOPOLOGY: linear (ii) MOLECULE TYPE: Other nucleic acid;
        (A) DESCRIPTION: Oligonucleotide (xi) SEQUENCE DESCRIPTION: SEQ ID NO: 3:

ACCTGTGAGG GCTGCAARGK YTTCTTCAA                              29

(2) INFORMATION FOR SEQ ID NO: 4:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Oligonucleotide (xi) SEQUENCE DESCRIPTION: SEQ ID NO: 4:

GGTTCAATGC ACT                                               13

(2) INFORMATION FOR SEQ ID NO: 5:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Oligonucleotide (xi) SEQUENCE DESCRIPTION: SEQ ID NO: 5:

CGTTCAATGC ACA                                               13

(2) INFORMATION FOR SEQ ID NO: 6:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Oligonucleotide (xi) SEQUENCE DESCRIPTION: SEQ ID NO: 6:

AGGTCAATGA CCT                                               13

(2) INFORMATION FOR SEQ ID NO: 7:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Oligonucleotide (xi) SEQUENCE DESCRIPTION: SEQ ID NO: 7:

AGAACAATGT TCT                                               13